(12) United States Patent
Jewell et al.

(10) Patent No.: US 9,410,207 B2
(45) Date of Patent: Aug. 9, 2016

(54) METHOD AND COMPOSITIONS FOR DETECTING EPIDERMAL GROWTH FACTOR RECEPTOR VARIANT FORMS IN CANCER CELLS

(71) Applicant: Abbott Molecular Inc., Des Plaines, IL (US)

(72) Inventors: Susan S. Jewell, Elmhurst, IL (US); John C. Russell, Chicago, IL (US); Larry E. Morrison, Phoenix, AZ (US)

(73) Assignee: Abbott Molecular Inc., Des Plaines, IL (US)

( * ) Notice: Subject to any disclaimer, the term of this patent is extended or adjusted under 35 U.S.C. 154(b) by 437 days.

(21) Appl. No.: 13/728,912

(22) Filed: Dec. 27, 2012

(65) Prior Publication Data

US 2013/0171641 A1   Jul. 4, 2013

Related U.S. Application Data

(60) Provisional application No. 61/582,103, filed on Dec. 30, 2011, provisional application No. 61/582,135, filed on Dec. 30, 2011.

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/156* (2013.01)

(58) Field of Classification Search
CPC ........... C12Q 1/6886; C12Q 2600/106; C12Q 2600/156
USPC ....................................................... 435/6.11
See application file for complete search history.

(56) References Cited

U.S. PATENT DOCUMENTS

2007/0207489 A1* 9/2007 Pestano et al. .................. 435/6
2011/0166409 A1   7/2011 Donovan et al.

OTHER PUBLICATIONS

Heimberger et al. Clinical Cancer Research. 2005. 11: 1462-1466.*
Ji et al. PNAS. 2006. 103(20): 7817-7822.*
Sampson et al. Journal of Clinical Oncology. 2010. 28(31): 4722-4729.*
Gajadhar et al. Mol. Cancer Res. 2012. 10(3): 428-440.*
Varella-Garcia et al. Diagnostic Pathology. 2006. I:19.*
Marquez (retrieved on Feb. 12, 2015 from the internet: http://tools.lifetechnologies.com/downloads/EGFRPoster_D452F.pdf).*

(Continued)

*Primary Examiner* — Juliet Switzer
*Assistant Examiner* — Joseph G Dauner
(74) *Attorney, Agent, or Firm* — Klintworth & Rozenblat IP LLC

(57) ABSTRACT

Method and compositions for screening for the presence of Epidermal Growth Factor Receptor variant 3 (EGFR(v3)) in a sample are described. The method comprises obtaining a sample containing a plurality of cells; hybridizing a set of chromosomal probes to the sample, wherein the set comprises an EGFR(v3)-probe and a probe to chromosome 7 different from an EGFR(v3)-probe; and visualizing the hybridization pattern of the set of chromosomal probes in the plurality of cells of the sample, wherein the presence of at least one copy of chromosome 7 lacking a hybridization signal of the EGFR (v3)-probe in at least one cell is indicative of the presence of the EGFR(v3) in the sample. The method and compositions are suitable for diagnosing the therapeutic outcome for treating a patient having a cancer with an anti-EGFR therapeutic agent and for screening a sample for a predisposition for forming an EGFR-associated cancer.

16 Claims, 1 Drawing Sheet

(56) References Cited

OTHER PUBLICATIONS

Wiegant et al. Current Protocols in Cytometry. 1997. 8.3.12-8.3.21.*
Supporting Information for Ji et al. PNAS. 2006. 103(20): 7817.*
Kuan et al. "EGF mutant receptor vIII as a molecular target in cancer therapy," Endocrine-Related Cancer, Jun. 1, 2001, vol. 8, pp. 83-96 (2001).
Malecki et al. "Isolation of single, intact chromosomes from single, selected ovarian cancer cells for in situ hybridization and sequencing," Gene, On-line publication date: Dec. 1, 2011, vol. 493, No. 1, pp. 132-139 (2012).
Guillaudeau et al. "Adult diffuse gliomas produce mRNA transcripts encoding EGFR isoforms lacking a tyrosine kinase domain," International Journal of Oncology, On-line publication date: Dec. 8, 2011, vol. 40, pp. 1142-1152 (2012).
International Search Report and Written Opinion of International Searching Authority mailed Apr. 5, 2013 for International Application No. PCT/US2012/072070.

* cited by examiner

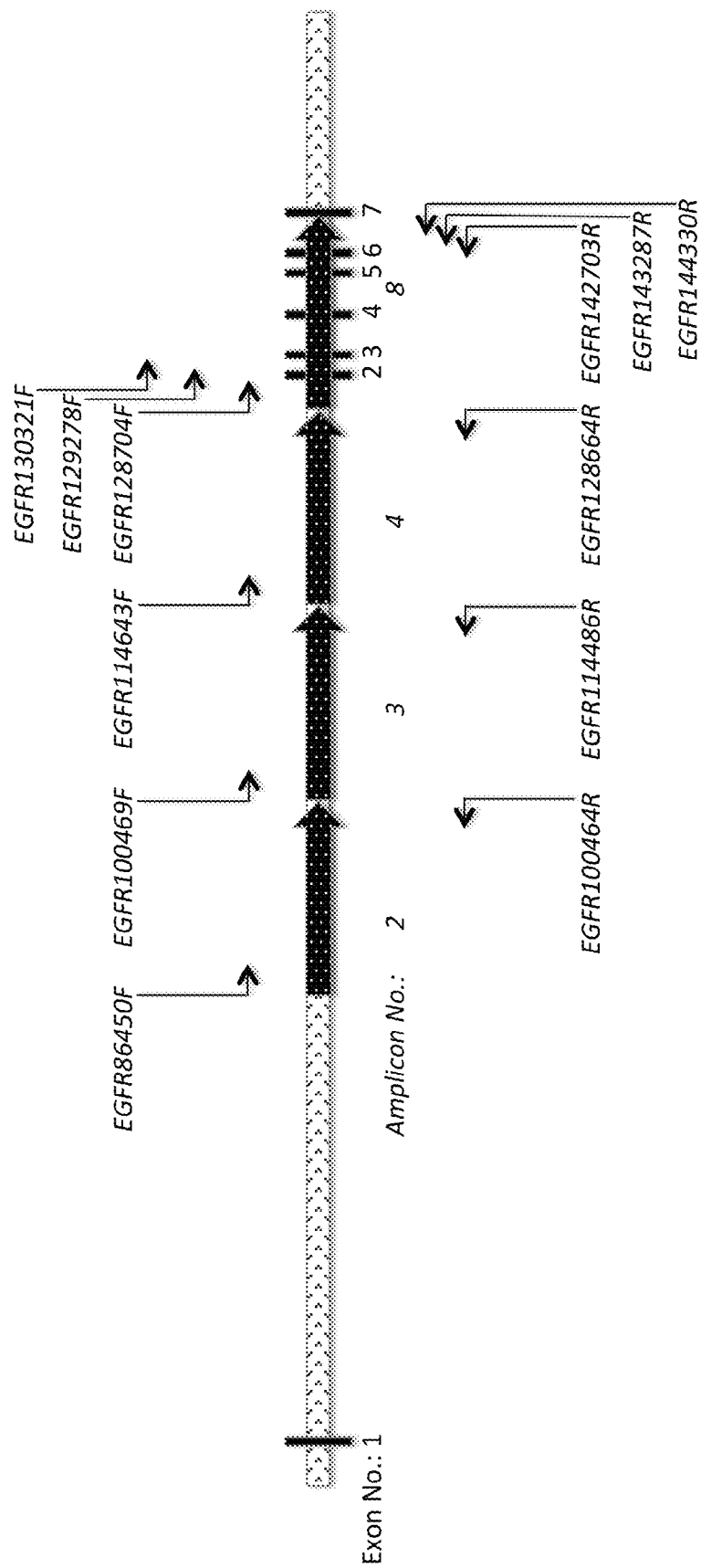

METHOD AND COMPOSITIONS FOR DETECTING EPIDERMAL GROWTH FACTOR RECEPTOR VARIANT FORMS IN CANCER CELLS

CROSS-REFERENCE TO RELATED APPLICATIONS

This application claims benefit of priority under 35 U.S.C. 119 to U.S. provisional patent application Ser. No. 61/582,103, filed Dec. 30, 2011, and entitled "METHOD AND COMPOSITIONS FOR DETECTING EPIDERMAL GROWTH FACTOR RECEPTOR VARIANT FORMS IN CANCER CELLS," and to U.S. provisional patent application Ser. No. 61/582,135, filed Dec. 30, 2011, and entitled "NUCLEIC ACID HYBRIDIZATION PROBES," to Russell et al., The contents of both these applications are herein incorporated by reference in their entireties.

SEQUENCE LISTING

The SEQ ID NOs. disclosed herein are included in the Sequence Listing found at the end of the specification and are included in a computer readable form entitled "ABT01-072-US [SEQUENCE LISTING]_ST25.text," filed by electronic means via the EFS-Web e-filing system, the contents of which are incorporated by reference in its entirety.

BACKGROUND OF THE INVENTION

Epidermal Growth Factor Receptor (EGFR) is a cell surface protein that binds to its ligand, epidermal growth factor (EGF) and related ligands, and controls cell growth and differentiation as a result of this receptor-ligand interaction. EGFR is a member of the tyrosine kinase superfamily of signaling molecules that participate in ligand-mediated, cell proliferation mechanisms. Like other members of the receptor tyrosine kinase family, EGFR is an oncogene that has an important role in tumorigenesis. Mutations in EGFR are associated with a variety of cancers, including, for example, adenocarcinoma, adrenocortical cancer, biliary cancer, breast cancer, cervical cancer, colorectal cancer, esophageal cancer, gall bladder cancer, gastric cancer, glioma, glioblastoma, and glioblastoma multiforme, head and neck cancer, lung cancer, pancreatic cancer, and salivary cancer.

Because of its importance in cell proliferation and its involvement as an oncogenic agent in cancers, considerable research interest has focused on understanding the mechanism of EGFR activation and signaling. The protein encoded by the EGFR gene is a transmembrane glycoprotein that possesses an extracellular ligand binding domain, a transmembrane domain, and an intracellular kinase domain. Upon binding to EGF or structurally related EGF-like molecules, EGFR undergoes protein dimerization and tyrosine autophosphorylation by the intracellular kinase domain that leads to receptor activation. Activated EGFR phosphorylates other cytoplasmic substrates as part of the signaling cascade, resulting in numerous changes in gene expression and cellular physiology, including anti-apoptosis and increased cell proliferation.

Mutations in the EGFR gene can lead to overexpression and/or inappropriate activation of the EGFR protein and potentially unchecked cell proliferation. A significant percentage of epithelial cancers are associated with mutation, rearrangement, and/or ectopic regulation of the EGFR gene. In addition, amplification of the EGFR gene occurs in many cancers. For example, EGFR gene amplification arises in at least 40% of malignant gliomas.

Although a number of oncogenic point mutations occur in the EGFR gene, the constitutively active deletion mutation known as EGFR variant III (EGFR(v3)) appears to be the most common activating mutation found to date. For example, EGFR(v3) is the most common deletion mutant expressed in malignant gliomas and has been reported to occur in almost half of such tumors. EGFR(v3) contains an in-frame deletion of exons 2 through 7 corresponding to amino acids 6 through 273. This gene produces a 140- to 145-kDa receptor with unique epitopes. Deletion of this coding information maps to the extracellular ligand-binding domain of EGFR(v3) and impacts the binding affinity of EGFR(v3) for EGF and related ligands. Although EGFR(v3) cannot bind ligand with high affinity, it is constitutively autophosphorylated. Consequently, EGFR(v3) is of substantial interest due to its effects on signal transduction and as a potential tumor-specific target.

EGFR is an attractive target for anticancer therapeutic agent development. EGFR gene amplification status in a given tumor may indicate whether cancer cells will respond to therapeutics directed to EGFR. And many of the tumors harboring an amplified EGFR gene produce a mutant EGFR protein. Thus, prognosis and therapeutic response may also depend upon whether the expressed EGFR gene is mutant or wild type.

In situ methods provide a powerful and sensitive means for detecting the presence of tumor-specific antigens in biological specimens. Several challenges remain for detecting in situ the presence of the EGFR(v3) gene products in tumors. The EGFR(v3) mRNA is difficult to detect in situ with reverse transcriptase-based PCR techniques, owing to the highly degraded state of RNA in formalin-fixed paraffin-embedded specimens. Antibodies directed against the EGFR(v3) protein are also poor for use in immunohistochemistry methodologies. Thus, the existing in situ methods are not amenable for efficiently detecting EGFR(v3) status in tumors.

SUMMARY

In a first aspect, the invention is a method of screening for the presence of EGFR(v3) in a sample. The method comprises obtaining a sample containing a plurality of cells; hybridizing a set of chromosomal probes to the sample, wherein the set comprises an EGFR(v3)-probe and a probe to chromosome 7 different from an EGFR(v3)-probe; and visualizing the hybridization pattern of the set of chromosomal probes in the plurality of cells of the sample. According to this aspect of the invention, the presence of at least one copy of chromosome 7 lacking a hybridization signal of the EGFR (v3)-probe in at least one cell is indicative of the presence of the EGFR(v3) in the sample.

In a second aspect, the invention is a method of diagnosing the therapeutic outcome for treating a patient having a cancer with an anti-EGFR therapeutic agent. The method comprises obtaining a sample containing a plurality of cancer cells; hybridizing a set of chromosomal probes to the sample, wherein the set comprises an EGFR(v3)-probe and a probe to chromosome 7 different from an EGFR(v3)-probe; and visualizing the hybridization pattern of the set of chromosomal probes in the plurality of cancer cells in the sample. According to this aspect of the invention, the presence of at least one copy of chromosome 7 lacking a hybridization signal of the EGFR(v3)-probe in at least one cancer cell is indicative of the cancer having EGFR(v3), wherein the cancer is predisposed to developing a resistance to treatment with the anti-EGFR therapeutic agent.

In a third aspect, the invention is a method of screening a sample for a predisposition for forming an EGFR-associated cancer. The method comprises obtaining a sample containing a plurality of cells; hybridizing a chromosomal probe to the sample, wherein the chromosomal probe is at least one member selected from the group consisting of a chromosome enumeration probe to chromosome 7, a chromosome arm probe to at least one arm of chromosome 7, and a locus specific probe to a gene or region of chromosome 7; and visualizing the hybridization pattern of the chromosomal probe in the plurality of cells of the sample. According to this aspect of the invention, the presence of three or more hybridization signals directed against chromosome 7 in at least one cell is indicative of amplification of chromosome 7 and of the sample being predisposed to forming an EGFR-associated cancer.

In a fourth aspect, the invention is a kit consisting of a set of chromosomal probes and optionally one or more reagents selected from the group consisting of a slide, phosphate buffered saline, hybridization buffer, 4,6-diamidino-2-phenylindole dihydrochloride, sodium chloride-sodium citrate solution, fixative, ethanol, non-ionic detergent, and denaturation buffer. According to this aspect of the invention, the set of chromosomal probes comprises an EGFR(v3) probe and at least one member selected from the group consisting of a CEP 7 probe, a 7p12 probe and an EGFR probe. Furthermore, the probes are labeled such that each probe can be distinctly visualized after hybridization to a biological sample.

BRIEF DESCRIPTION OF THE DRAWINGS

FIG. 1 illustrates a schematic of the EGFR gene in the region of the deletion for EGFR(v3) and the amplicons selected for FISH analysis. The exons are denoted as solid vertical black bars and are labeled 1-7(non-italicized) below the depiction of the EGFR gene sequence (white stippled region). Exemplary amplicons (depicted by the black stippled arrows) are denoted by an italicized number (e.g., 1, 2, and 8) below the numeric designations for the exons. The following amplicons were amplified with the following oligonucleotide primer pairs: Amplicon 1: EGFR72397F ( SEQ. ID NO:1) and EGFR86421R ( SEQ ID NO:2); Amplicon 2: EGFR86450F ( SEQ. ID NO:3) and EGFR100464R ( SEQ ID NO:4); Amplicon 3: EGFR100469F ( SEQ. ID NO:5) and EGFR114486R ( SEQ ID NO:6); Amplicon 4: EGFR114643F ( SEQ. ID NO:7) and EGFR128664R ( SEQ ID NO:8); Amplicon 5: EGFR128704F ( SEQ. ID NO:9) and EGFR142703R ( SEQ ID NO:10); Amplicon 6: EGFR129278F ( SEQ. ID NO:11) and EGFR143287R ( SEQ ID NO:12); Amplicon 7: EGFR130321F ( SEQ. ID NO:13) and EGFR144330R ( SEQ ID NO:14); and Amplicon 8: EGFR128704F ( SEQ. ID NO:9) and EGFR144330R ( SEQ ID NO:14). The relative locations and the orientations of the oligonucleotide primers for their use are denoted by positions of the directional arrows associated with each identified oligonucleotide primer.

DETAILED DESCRIPTION

The invention provides improved in situ methods for detecting amplified EGFR genes in biological samples for the purpose of detecting EGFR(v3) in EGFR-associated cancers and screening subjects at risk for these cancers. The described methods also have utility for monitoring patients diagnosed with cancer, for assessing prognosis of an effective therapeutic response directed against cancers containing EGFR deletion mutations, particularly EGFR(v3). For example, the methods enable a physician to diagnose the therapeutic outcome for treating a patient having a cancer with an anti-EGFR therapeutic agent, particularly for cancers that are predisposed to developing resistance to anti-EGFR therapeutic agents. The disclosed methods also have utility for monitoring patients diagnosed with cancer and for evaluating tumor recurrence.

As used herein, "an EFGR-associated cancer" is a cancer comprising cells having increased expression of EGFR, possessing amplified copies of chromosome 7, and/or encoding a genetic alteration of the chromosomal locus encoding EGFR. Cells of such cancers display enhanced proliferation rates in the presence of EGF and EGF-related ligands and possess elevated levels of gene products that are regulated by EGFR-mediated signaling activities.

The insight recognized by the inventors was that chromosomal DNA may be probed directly using in situ methods to detect the presence of amplified and/or deletion mutations of EGFR without having to resort to independent evaluation of EGFR gene product status at the mRNA or protein levels. The disclosed methods are simple and robust and provide a reproducible, sensitive indication of the EGFR gene status in cells.

In general, a set of chromosomal probes is hybridized to the chromosomes of cells from a biological sample on a slide. The resultant hybridization pattern produced in the biological sample is then visualized using suitable cytogenetic techniques, wherein the amplification status of EGFR and the presence of EGFR(v3) may be discerned.

In Situ Hybridization

The presence or absence of cells containing amplified EGFR and/or EGFR(v3) is determined by in situ hybridization. In general, in situ hybridization includes the steps of fixing a biological sample, hybridizing a chromosomal probe to target DNA contained within the fixed biological sample, washing to remove non-specific binding, and detecting the hybridized probe.

The EGFR gene spans 186 kbp on chromosome 7 at cytogenetic band 7p12 (Entrez Gene reference system). As explained previously, EGFR(v3) is an in-frame deletion variant of the wild-type EGFR gene ("EGFR(wt)") that lacks exons 2-7, including the intervening introns contained between exons 2 and 7 (that is, introns ##2-6). Removal of substantial portions of intron 1 and intron 7 often accompanies deletion of exons 2-7. Accordingly, the presence of EGFR(v3) in the cell may be discerned by whether 12 kbp-135 kbp of unique chromosomal DNA is present or absent at cytogenetic band 7p12 of chromosome 7.

A "biological sample" is a sample that contains cells or cellular material. Typically, the biological sample is concentrated prior to hybridization to increase cell density. Non-limiting examples of biological samples include urine, blood, cerebrospinal fluid (CSF), pleural fluid, sputum, and peritoneal fluid, bladder washings, secretions (for example, breast secretion), oral washings, tissue samples (for example, a biopsy), touch preps, or fine-needle aspirates. The type of biological sample that is used in the methods described herein depends on the type of cancer one wishes to detect. For example, urine and bladder washings provide useful biological samples for the detection of bladder cancer and to a lesser extent prostate or kidney cancer. Pleural fluid is useful for detecting lung cancer, mesothelioma or metastatic tumors (for example, breast cancer), and blood is a useful biological sample for detecting leukemia. A biopsy is useful for detecting gliomas. For tissue samples, the tissue can be fixed and placed in paraffin for sectioning, or frozen and cut into thin sections. Optionally, tissue samples can be dispersed into single cells by trypsin treatment or any other means of disrupting extracellular connections between cells.

Cells are typically harvested from a biological sample using standard techniques. For example, cells can be harvested by centrifuging a biological sample to collect the cells as a pellet.

The cells of the pellet are usually washed in phosphate-buffered saline (PBS). The cells are suspended in PBS and re-collected by centrifugation. The cells can be fixed, for example, in acid alcohol solutions, acid acetone solutions, or aldehydes such as formaldehyde, paraformaldehyde, and glutaraldehyde. For example, a fixative containing methanol and glacial acetic acid in a 3:1 ratio, respectively, can be used as a fixative. A neutral buffered formalin solution also can be used, and includes approximately 1% to 10% of 37-40% formaldehyde in an aqueous solution of sodium phosphate. Slides containing the cells can be prepared by removing a majority of the fixative, leaving the concentrated cells suspended in only a portion of the solution.

The cell suspension is applied to slides such that the cells do not overlap on the slide. Cell density can be measured by a light or phase contrast microscope. For example, cells harvested from a 20 to 100 ml urine sample typically are suspended in a final volume of about 100 to 200 µl of fixative. Three volumes of this suspension (usually 3, 10, and 30 µl), are then dropped into 6 mm wells of a slide. The density of cells in these wells is then assessed with a phase contrast microscope. If the well containing the greatest volume of cell suspension does not have enough cells, the cell suspension is concentrated and placed in another well.

Prior to in situ hybridization, chromosomal probes and chromosomal DNA contained within the cell each are denatured. Denaturation process is performed in several ways. For example, denaturation can be effected with buffered solutions having elevated pH, with elevated temperatures (for example, temperatures from about 70° C. to about 95° C.), or with organic solvents such as formamide and tetraalkylammonium halides, or combinations thereof. For example, chromosomal DNA can be denatured by a combination of temperatures above 70° C. (for example, about 73° C.) and a denaturation buffer containing 70% formamide and 2×SSC (0.3M sodium chloride and 0.03 M sodium citrate). Denaturation conditions typically are established such that cell morphology is preserved. Chromosomal probes can be denatured by heat. For example, probes can be heated to about 73° C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. The greater the concentration of probe, the greater the probability of forming a hybrid. For example, in situ hybridizations are typically performed in hybridization buffer containing 1-2×SSC, 50% formamide and blocking DNA to suppress non-specific hybridization. In general, hybridization conditions, as described above, include temperatures of about 25° C. to about 55° C., and incubation lengths of about 0.5 hours to about 96 hours. More particularly, hybridization can be performed at about 32° C. to about 40° C. for about 2 to about 16 hours.

Non-specific binding of chromosomal probes to DNA outside of the target region can be removed by a series of washes. Temperature and concentration of salt in each wash depend on the desired stringency. For example, for high stringency conditions, washes can be carried out at about 65° C. to about 80° C., using 0.2×SSC to about 2×SSC, and about 0.1% to about 1% of a non-ionic detergent such as Nonidet P-40 (NP40). Stringency can be lowered by decreasing the temperature of the washes or by increasing the concentration of salt in the washes.

Chromosomal Probes

Suitable probes for use in the in situ hybridization methods utilized with the invention fall into two broad groups: chromosome enumeration probes and locus-specific probes. Chromosomal enumeration probes are probes that hybridize to a chromosomal region, usually a repeat sequence region, and indicate the presence or absence of an entire chromosome. Locus-specific probes are probes that hybridize to a specific locus on a chromosome and detect the presence or absence of a specific locus. Chromosome arm probes are probes that fall between these two broad groups. The probes belonging to this category hybridize to a chromosomal region and indicate the presence or absence of an arm of a specific chromosome. For example, a 7p chromosomal arm probe comprises a sequence isolated from the region between the telomere of the p arm of chromosome 7 and the centromere of chromosome 7.

As is well known in the art, a chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs that are referred to as alpha-satellite DNA. To detect amplification of chromosome 7 according the present invention, preferred target sequences include the repetitive DNA associated with the centromere of this chromosome. Thus, preferred hybridization probes include chromosome enumeration probes that hybridize to centromeric DNA of chromosome 7. Examples of chromosome enumeration probes are described in the Tables and Examples.

A locus-specific probe hybridizes to a specific, non-repetitive genetic locus on a chromosome. Preferred locus-specific probes hybridize to the 7p12 cytogenetic band region of chromosome 7. Even more preferable locus-specific probes include EGFR gene sequences within the 7p12 cytogenetic band region. Specifically, highly preferred locus-specific probes include those that hybridize to target chromosomal DNA common to both EGFR(wt) and EGFR(v3). Such highly preferred locus-specific probes include probes that hybridize to target chromosomal DNA of the EGFR gene at any of exon 1, exons 8 through 28, introns 8 through 27, and/or the flanking DNA sequences lying immediately 5' and/or 3' of the EGFR gene (that is, upstream of exon 1 and/or downstream of exon 28).

To discern the deletion mutation status of EGFR of chromosome 7 as being EGFR(v3), preferred locus-specific probes are selected, wherein such probes hybridize to one or more EGFR-specific DNA sequences at any of exons 2, 3, 4, 5, 6 and 7, introns 2, 3, 4, 5, and 6, or combinations thereof. These particular DNA sequences are preferred for use as probes in this regard because these sequences are present in EGFR(wt) and absent in EGFR(v3). Thus, the status of EGFR (v3) in a cell can be discerned by the relative absence of a hybridization signal on chromosome 7 when contacted with locus-specific probes directed to the deleted sequences of EGFR(v3).

As described above, sequences associated with portions of intron 1 and intron 7 of EGFR(wt) are also deleted in EGFR (v3). These deleted intron sequences are also suitable for use as chromosomal probes of the present invention. Example 1 provides an illustration of preferred chromosomal probes directed to deleted sequences of EGFR(v3) that fall within these intronic sequences.

In other preferred embodiments, locus-specific probes may comprise a plurality of discrete DNA sequences from a particular genetic locus. For example, a probe specific for one or more of any of the deleted exons or introns of EGFR(v3) can comprise a plurality of discrete DNA sequences, wherein each DNA sequence hybridizes to one or more EGFR-specific DNA sequences at any of exons 2, 3, 4, 5, 6 and 7, introns 2, 3, 4, 5, and 6, or combinations thereof and wherein each DNA sequence has a length of at least 50 base-pairs.

Chromosomal probes are chosen for maximal sensitivity and specificity. Using a set of chromosomal probes (that is, two or more probes) provides greater sensitivity and specificity than use of any one chromosomal probe. Thus, chromosomal probes that detect both EGFR gene amplification status and the presence of EGFR(v3) are included in a set. For example, a set of chromosomal probes can include chromosome enumeration probe to chromosome 7 (for example, a CEP 7 probe) and a locus-specific probe specific for one or more of any of the deleted exons or introns of EGFR(v3) ("EGFR(v3)-probe"). Alternatively, a set of chromosomal probes can include two different locus-specific probes, wherein the first locus-specific probe hybridizes to chromosome 7 at a locus other than EGFR and the second locus-specific probe is an EGFR(v3)-probe. Additionally, the foregoing examples of probe sets can include a third probe specific for one or more chromosomal sequences common to both EGFR(wt) and EGFR(v3) ("EGFR-probe"). Examples of an EGFR-probe include any one or more of the following sequences or combinations thereof: 5'-flanking sequences immediately upstream of exon 1; exon 1, any of exons 8 through 28, any of introns 7 through 27; and 3'-flanking sequences immediately downstream of exon 28.

The present invention is directed to measuring amplification of chromosome 7 and loss of chromosomal sequences within EGFR in biological samples. Such measurements pose unique challenges that the skilled artisan would recognize and control for. For example, it is generally easier to measure gain of a target chromosome or chromosome region due to an amplification event than to measure loss of a target chromosome or chromosome region due to a deletion event. The difficulty in measuring loss of chromosome sequence information is confounded by the possible occurrence of failed or poor hybridization in cells that falsely suggests loss. Probe designs that contain overlapping sequence content for detecting both retained and deleted sequence information may also confound the analysis by hybridizing to a chromosomal region flanking a deletion that falsely suggests no loss.

The latter problem can be addressed by appropriate probe design. Probes that are designed to detect a deletion event ("deletion probes"), such as an EGFR(v3)-probe, are designed not to extend beyond the minimally deleted region. If too much of the deletion probe extends beyond the deleted sequence, enough signal may be produced in the hybridization assay to be falsely counted. For this reason, locus-specific probes designed to detect deletions are generally smaller than locus-specific probes designed to detect gains.

The former problem of failed or poor hybridization can be addressed in several ways. One approach is to include in the hybridization assay a control probe that provides a positive hybridization signal for the presence of undeleted regions of the specific locus under study (for example, an EGFR-probe if EGFR is the locus under study). Whenever possible, such control probes are designed to have the length and sequence complexity of the deletion probes. This probe design will aid in yielding comparable hybridization signal intensities for deletion probes and control probes in samples that contain sequences for both probes. Another approach is to include control biological samples known to contain undeleted locus-specific information so that one can confirm under comparable hybridization conditions that the deletion probe hybridizes appropriately to those samples.

Since deletion probes are usually kept small their signals are not as intense as signals for targets typically gained. This in turn makes it more likely that real signals from targets being monitored for deletion may be miscounted. Likewise, some chromosome enumeration probes usually provide brighter signals and hybridize faster than locus-specific probes. Differences in apparent hybridization signal intensity can be compensated for by choosing appropriate probe design and biological samples, and by pre-calibrating the signal intensity of probes hybridized with control biological samples. These considerations are taken into account when selecting a probe set and biological samples for practicing the present invention.

Chromosome enumeration probes and locus-specific probes are available commercial vendors. Examples of chromosome enumeration probes to chromosome 7 are presented in the Examples. Alternatively, probes can be made non-commercially from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). Probes less than 100-200 nucleotides in length may also be prepared by in vitro chemical synthesis methods.

The probes of the present invention comprise DNA having a preferred length of 50-10,000 base-pairs. In some preferred embodiments, such probes comprise DNA having a preferred length of 100-5,000 base-pairs. In other preferred embodiments, such probes comprise DNA having 200-2,500 base-pairs.

The choice of probe length and design is often tied to considerations of the manner whereby the probes are labeled with a detectable moiety. Labeling design considerations are selected to maximize the amount of label incorporated per unit length of the probe, which is often referred to as the specific activity of the labeled probe. For relatively small probes, such as probes less than 200 nucleotides in length or probes that are prepared by chemical means, chemical or enzymatic end-labeling one or both termini of the probe is a preferred method of labeling. For example, carboxytetramethylrhodamine (CTMR) is a preferred chemical labeling reagent for this purpose. For longer probes, such as probes greater than 100 nucleotides in length or probes can be prepared by enzymatic amplification means, for example, with the polymerase chain reaction (PCR), a preferred method of labeling is nick-translation or PCR-labeling using labeled deoxynucleotide triphosphates. One skilled in the art would recognize that these labeling methods are described for illustrative purposes and that any method of incorporating a label into a nucleic acid would represent an acceptable means of preparing labeled probes of the present invention.

As explained above, probes that include non-repetitive genetic locus information are preferred embodiments of a locus-specific probe. In FISH hybridization applications, it can be important to further refine the target sequences to exclude certain repetitive sequence elements found ubiquitously in natural sequences. In this regard, one can select a priori the precise boundaries and composition of the desired target sequences by virtue of PCR primer design that specifies the PCR products to be generated. For example, one can analyze a genetic locus or plurality of genetic loci from a given chromosomal region of interest to delineate non-repetitive genetic information (for example, gene-coding information) from repetitive sequence elements found dispersed throughout all chromosomal DNA (for example, SINEs, LINEs, and LTRs). Once delineated, one can then design PCR primers that can be used to amplify only the non-repetitive genetic information (that is, sequences lacking repetitive sequence elements as defined above) as the preferred target sequences. In many cases, the preferred target sequences can range in size from about 100bp about 6 kbp. Such non-repetitive sequence material is preferred for use in FISH applications, because the resultant probes generated from non-repetitive sequence element DNA obviates or at least substantially reduces the need to include $C_o$t-1 DNA in FISH applications, the latter of which reduces signal intensity and robustness. Once obtained, these non-repetitive sequences can be isolated or purified for use as substrates for preparing PCR-generated probes according to the methods outlined above.

Related nucleic hybridization probes for this purpose can be accomplished using the methods disclosed in U.S. patent application Ser. No. 13/728,975, filed simultaneously to this application, entitled NUCLEIC ACID HYBRIDIZATION PROBES to Russell et al. and now published as U.S. Patent Application Publication US 2013/0237437 A1, which claims benefit of priority to U.S. provisional patent application Ser. No. 61/582,135, filed Dec. 30, 2011, the contents of each application are herein incorporated by reference in their entireties.

Chromosomal probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

Fluorophores of different colors are chosen such that each chromosomal probe in the set can be distinctly visualized. For example, a combination of the following fluorophores may be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.).

Probes are visualized with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the chromosomal probes.

Probes also can be indirectly labeled with biotin or digoxygenin, or labeled with radioactive isotopes such as $^{32}$P and $^{3}$H, although secondary detection molecules or further processing then is required to visualize the probes. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard calorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

According to the present invention, a preferred method of detecting the hybridization signals by chromosomal probes in cells of a biological sample is in situ fluorescence hybridization (FISH) with a set of fluorescently labeled probes. Each probe is distinguished from other probes based upon different fluorescent labels attached to the probes. Examples of probe sets are described Example 1.

Fluorescent labels are visualized by any suitable means of detecting fluorescence. Preferably, the labels are visualized with fluorescence microscopy and appropriate filters. Because the loss of a specific hybridization signal at the EGFR locus of chromosome 7 is diagnostic for the presence of EGFR(v3), it is preferable to quantitatively measure the intensity of the hybridization signals with digital imaging. Such techniques and automated digital imaging systems are well known in the art.

Selection of Cells

According to the invention, cells are microscopically selected from the cells of a biological sample (for example, urine) on a slide prior to chromosomal analysis. "Selecting" refers to the identification of cells that are more likely to be neoplastic due to one or more cytologic (mainly nuclear) abnormalities such as nuclear enlargement, nuclear irregularity or abnormal nuclear staining (usually a mottled staining pattern). These nuclear features, can be assessed with nucleic acid stains or dyes such as propidium iodide or 4,6-diamidino-2-phenylindole dihydrochloride (DAPI). Propidium iodide is a red-fluorescing DNA-specific dye that can be observed at an emission peak wavelength of 614 nm. Typically, propidium iodide is used at a concentration of about 0.4 µg/ml to about 5 µg/ml. DAPI, a blue fluorescing DNA-specific stain that can be observed at an emission peak wavelength of 452 nm, generally is used at a concentration ranging from about 125 ng/ml to about 1000 ng/ml. Staining of cells with DAPI or propidium iodide is generally performed after in situ hybridization is performed.

Determining Presence of Cells Having Amplified Chromosome 7

After cells are selected based on one or more of the stated criteria, the presence or absence of chromosome 7 amplification is assessed by examining the hybridization pattern of the chromosomal probes (that is, the number of signals for each probe) in each selected cell and recording the number of chromosome signals. Chromosome 7 amplification will be revealed by the presence of greater than two hybridization signals per cell nucleus when analyzed with a probe set that includes a chromosome 7-specific probe (for example, a CEP 7 probe or any locus-specific probe to a chromosome 7 gene or region). This step is repeated until the hybridization pattern has been assessed in at least 4 cells that contain amplified chromosome 7. In a typical assay, the hybridization pattern is assessed in about 20 to about 25 selected cells, or a sufficient number of cells to permit an adequate statistical analysis of the resultant hybridization data.

Determining Presence of Cells Having EGFR(v3)

Cells with more than two copies of chromosome 7 are considered predisposed to having an EGFR mutation. To evaluate whether the cells contain EGFR(v3), cells are analyzed with a chromosomal probe set comprising a first probe and a second probe. The first probe comprises a chromosome 7-specific probe other than an EGFR(v3)-probe (for example, a CEP 7 probe or an EGFR-probe). The second probe comprises an EGFR(v3)-probe.

The first probe identifies all copies of chromosome 7 present in a given cell regardless of the status of EGFR. The second probe identifies whether deleted exon information of EGFR(v3) is present or absent in the resident EGFR gene of each chromosome 7 for that cell.

Cells lacking EGFR(v3) have each copy of chromosome 7 hybridized to both probes. Cells containing EGFR(v3) have at least one copy of chromosome 7 that fails to hybridize to only the EGFR(v3)-probe. Thus, the presence of EGFR(v3) in a given cell will be discerned by the presence of at least one copy of chromosome 7 lacking a hybridization signal to only the EGFR(v3)-probe.

The sensitivity and accuracy of the foregoing analysis is improved by including a third probe directed to a region of chromosome 7 other than the centromere. A preferred probe is one that hybridizes to sequences at cytogenetic band 7p12 ("7p12-probe"). A preferred 7p12-probe for this purpose is an EGFR-probe. Accordingly, the amplification status of chromosome 7, as well as the presence of sequences associated with EGFR, may be confirmed by detecting an independent hybridization signal with an EGFR-probe.

Monitoring Patients for EGFR-Associated Cancer

The superior sensitivity of the methods described herein is amenable for detecting and monitoring of cancers associated with amplification of chromosome 7 and EGFR(v3) status. A patient with a glioma or other type of cancer may have increased chromosome 7 ploidy (that is, amplification of chromosome 7 beyond the two copies normally present in a somatic cell) and EGFR(v3). The application of the methods and compositions of the present invention provides an effective means to monitor treatment efficacy directed to EGFR. For example, the method enables the physician to diagnose the therapeutic outcome for treating a patient having a cancer with an anti-EGFR therapeutic agent, particularly for cancers that are predisposed to developing resistance to anti-EGFR therapeutic agents. The method of the present invention enables a physician to confirm the presence of EGFR(v3) in cancer cells, thereby permitting the physician to develop an alternative treatment strategy as warranted. The methods and compositions of the present invention also enable one to survey for tumor recurrence/progression in patients with EGFR-associated cancers. An EFGR-associated cancer for which the described methods and compositions of the invention may be used includes adenocarcinoma, adrenocortical cancer, biliary cancer, breast cancer, cervical cancer, colorectal cancer, esophageal cancer, gall bladder cancer, gastric cancer, glioma, glioblastoma, and glioblastoma multiforme, head and neck cancer, lung cancer, pancreatic cancer, and salivary cancer.

The invention will be further described in the following examples, which do not limit the scope of the invention described in the claims.

EXAMPLES

Example 1

Probe Preparation

Primers specific to EGFR were designed for amplification of sequence encompassing the EGFR variant 3. Primers were designed to have a high $T_M$ to promote specificity and with restriction sites at the 5' end for cloning of the PCR products. Primers in combination with BAC DNA containing EGFR sequences were used to amplify specific regions of the EGFR gene such that one amplicon (#8) covered exons two through seven (see FIG. 1). Other primer combinations were used to amplify successive regions upstream of amplicon 8 (for example, amplicons 2, 3 and 4; see FIG. 1). The primers used for amplifying each of the amplicons illustrated in FIG. 1 are illustrated in Table 1 below. As inferred from Table 1, amplicon 8 corresponds to the region spanning amplicons 5-7 of FIG. 1.

TABLE 1

EGFR Amplicon Amplification Primer Sets

| SEQ ID NO. | SEQUENCE (5'→3') | Amplicon Target |
|---|---|---|
| 1 | CATCATCCGCGGAAGGATGCACAATCCTACATGCCCC | 1-Forward |
| 2 | CATCATATCGATCCTGGTGAACACAACCGGAGAATTAAA | 1-Reverse |
| 3 | CGGATCCTGTGTACCCCATGTGTTTAAATTTGCTG | 2-Forward |
| 4 | CAGGTACCTTCTTGGGTTAGCAGTGATCAAGTCACA | 2-Reverse |
| 5 | CAACTAGTATAAAGCAGAAGCATGTATCCAGGTTGC | 3-Forward |
| 6 | CCTCGAGCAAGCCTTGGCCCAGGCTTATTC | 3-Reverse |
| 7 | CATCATCCGCGGCATGAAATCTGCATTATCATCATCTGCA | 4-Forward |
| 8 | CATCATATCGATGCATATGGACTTACTCAAATGTTGGCCA | 4-Reverse |
| 9 | CGGATCCTATAGAGTGGCTGACATCCCCTAACGTG | 5-Forward |
| 10 | CCTCGAGACTTGCCACGGCAGCGCC | 5-Reverse |
| 11 | CATCGCGGCCGCACCATTTTCATATTTGAGGAAAGCATGG | 6-Forward |
| 12 | CCTCGAGTGGTGGAGGAGCCGAGGGATC | 6-Reverse |
| 13 | CATCGCGGCCGCTTCTTTGGTTCAGCTGAGAGAAACTTGC | 7-Forward |
| 14 | CCTCGAGCAGGGCTCAGCAGGAGACAGAGC | 7-Reverse |
| 9 | CGGATCCTATAGAGTGGCTGACATCCCCTAACGTG | 8-Forward |
| 14 | CCTCGAGCAGGGCTCAGCAGGAGACAGAGC | 8-Reverse |

The amplicons were prepared by PCR using the following PCR conditions. The PCR reaction conditions were performed in 1× Herculase buffer containing 3% DMSO, 500 µM dNTP, 0.5 µM each primer and 10 U Herculase. The PCR amplification conditions were as follows: (1) 92° C. for 2 minutes hot start; (2) ten cycles of: (a) 92° C. for 10 seconds, (b1) 64° (amplicons 3 and 4) or (b2) 68° C. (amplicons 2 and 8) for 10 minutes; twenty-five cycles of: 92° C. for 10 seconds; (c1) 64° (amplicons 3 and 4) or (c2) 68° C. (amplicons 2 and 8) for 10 minutes plus 10 second for successive cycles; and (3) 68° C. for 7 minutes.

Once amplified, PCR products were either nick-translated or chemically labeled with CTMR (providing an orange color). The full-length EGFR probe was labeled in green using a nick translation kit. The CEP-7 probe was labeled in aqua using a nick translation kit.

FISH Method for Detecting EGFR and EGFR(v3) Status

The probes were used to hybridize to paraffin sections of glioma specimens following pretreatment with Hopmann's paraffin pretreatment reagent.

Hybridization was performed with the HYBrite method or a conventional method. In the HYBrite method, a HYBrite™ system from Abbott Molecular (Downers Grove, Ill.) was used. Slides were placed on the HYBrite, and about 10 μl of the probe set was added, covered and sealed. The HYBrite was programmed as follows: 73° C. for 5 min, then 37° C. for 16 hr. Slides were washed with 0.4×SSC (0.06 M sodium chloride/0.006 M sodium citrate)/0.3% NP-40 at 73° C. for 2 min., rinsed with 2×SSC/0.1% NP40 at room temperature for 2 min. and air dried. Slides were counter-stained with approximately 10 μl of DAPI II (125 ng/ml of 4,6-diamidino-2-phenylindole dihydrochloride).

In the conventional method (that is, Coplin jar method), a master mix containing chromosome probes was prepared in hybridization buffer containing 50% formamide, 2×SSC, 0.5 μg/ml Cot1 DNA, and 2 μg/ml HP DNA. The probe mix was denatured at 73° C. for 5 min., and slides were denatured in denaturation buffer (70% formamide, 2×SSC) in a Coplin jar at 73° C. for 5 min (6-8 slides/jar). Slides were rinsed in each of 70%, 85%, and 100% ethanol for 1 min. Approximately 10 μl of hybridization mix was applied to each slide, covered with a cover slip, and sealed with rubber cement. Hybridization was performed in a humidified chamber at 37° C. overnight. Slides were washed in 0.4×SSC/0.3% NP-40 at 73° C. for 2 min., then rinsed briefly in 2×SSC/0.1% NP-40 at room temperature. After the slides are air-dried, slides were counter-stained with DAPI II. Samples were enumerated by recording the number of FISH signals in 100 consecutive cells.

An aqua filter was used to visualize the CEP 7 probe. Individual green and orange filters were used to visualize the EGFR-probe and EGFR(v3)-probe, respectively.

The results of the FISH analyses indicated that Amplicons 4 and 8 provided the strongest and cleanest signals for detecting the absence or presence of the EGFR(v3) deletion sequences. FISH analyses were performed using these amplicons as single probes or as probe mixtures when used in combination with full-length EGFR probe and CEP 7 probe.

Example 2

Samples and Sample Preparation

Samples will include tissue from 20 biopsy proven glioma cancer cases, in which a diagnosis is made by either positive cytology or by histology, in the case of cytology negative samples. Control samples will include ten blood samples from normal healthy donors (age 25-80).

Approximately 50 mg of glioma tissue material will be collected per patient and treated with trypsin to generate single cell suspensions. Five mL of blood will collected from the healthy donors. The samples will be stored at 4° C. for less than 48 hr, and processed by centrifugation at 1200×g for 5 min. The supernatant will be discarded, and the pellet will be suspended in 10 ml of 0.075 M KCl, and incubated at room temperature for 15 minutes. Samples will be processed by centrifugation at 1200×g for 5 min. to remove the KCl solution. The resultant pellets will be suspended in 10 ml of a 3:1 methanol:glacial acetic acid fixative, and processed by centrifugation at 1200×g for 5 min. The fixative will be carefully removed leaving the cell pellet, and this step will be repeated two more times.

Density of the cells on the slides will be monitored by frequently checking the slides between droppings using a phase contrast microscope fitted a 20× power objective. As many cells as possible will be loaded onto the slide without having cell overlap. Slides will be dried overnight at room temperature.

Slides containing the samples will be incubated in 2×SSC at 37° C. for 10-30 min. The slides will then be incubated in 0.2 mg/ml pepsin at 37° C. for 20 min. Slides will be subsequently washed twice in PBS at room temperature for 2 min. Cells will be fixed in 2.5% Neutral Buffered Formalin at room temperature for 5 min. Slides will be subsequently washed twice in PBS at room temperature for 2 min. The slides will be subjected to dehydration by successive contact in solutions of 70%, 85%, and 100% ethanol at room temperature for 1 min. The slides will be used immediately thereafter or stored at room temperature in the dark.

FISH Method for Detecting Chromosome 7 Amplification and EGFR

Three multicolor probe sets: A, B, and C will be used in the initial hybridizations. Probe sets A-C will contain the centromeric/locus-specific probes shown in Table 2. The color of the fluorophore used to label each probe is also shown in Table 2. An aqua filter will be used to visualize the CEP 7 probe. A dual green/red filter or individual green and orange filters will be used to visualize the EGFR-probe and EGFR (v3)-probe, respectively. An red filter will be used to visualize the 7p12 probe.

TABLE 2

FISH Probe Sets

| Probe Set | Spectrum Aqua | Spectrum Orange | Spectrum Green | Spectrum Red |
|---|---|---|---|---|
| A | CEP 7 | EGFR(v3) | EGFR | |
| B | CEP 7 | EGFR(v3) | | 7p12 |
| C | | EGFR(v3) | EGFR | |

Hybridization will be performed with the HYBrite method or a conventional method. In the HYBrite method, a HYBrite™ system from Abbott Molecular (Downers Grove, Ill.) will be used. Slides will be placed on the HYBrite, and about 10 μl of the probe set will be added, covered, and sealed. The HYBrite will be programmed as follows: 73° C. for 5 min, then 37° C. for 16 hr. Slides will then be washed with 0.4×SSC (0.06 M sodium chloride/0.006 M sodium citrate)/ 0.3% NP-40 at 73° C. for 2 min., rinsed with 2×SSC/0.1% NP40 at room temperature for 2 min., and air dried. Slides will be counter-stained with approximately 10 μl of DAPI II (125 ng/ml of 4,6-diamidino-2-phenylindole dihydrochloride).

In the conventional method (that is, Coplin jar method), a master mix containing chromosome probes will be prepared in hybridization buffer containing 50% formamide, 2×SSC, 0.5 μg/ml Cot1 DNA, and 2 μg/ml HP DNA. The probe mix will be denatured at 73° C. for 5 min., and slides will be denatured in denaturation buffer (70% formamide, 2×SSC) in a Coplin jar at 73° C. for 5 min (6-8 slides/jar). Slides will be rinsed in each of 70%, 85%, and 100% ethanol for 1 minute. Approximately 10 µl of hybridization mix will be applied to each slide, covered with a cover slip, and sealed with rubber cement. Hybridization will be performed in a humidified chamber at 37° C. overnight. Slides will be washed in 0.4× SSC/0.3% NP-40 at 73° C. for 2 min., then rinsed briefly in 2×SSC/0.1% NP-40 at room temperature. After the slides are air-dried, slides will be counter-stained with DAPI II. Samples will be enumerated by recording the number of FISH signals in 100 consecutive cells.

Other Embodiments

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of screening for the presence of EGFR(v3) in a sample, the method comprising:
   (a) obtaining a sample containing a plurality of cells;
   (b) hybridizing a set of chromosomal probes to the sample, wherein the set comprises an EGFR (v3)-probe and a probe to chromosome 7 different from an EGFR(v3)-probe; and
   (c) visualizing a hybridization pattern of the set of chromosomal probes in the plurality of cells of the sample, wherein the hybridization pattern comprises a presence of a signal from the probe to chromosome 7 different from an EGFR(v3)-probe and an absence of a signal from the EGFR(v3)-probe in at least one cell,
   wherein the EGFR(v3)-probe is labeled amplicon 4 prepared according to the following procedure:
      (i) contacting a DNA comprising a sequence encoding a wild-type EGFR gene with isolated oligonucleotide primers corresponding to SEQ ID NO:7 and SEQ ID NO:8;
      (ii) amplifying a portion of the sequence encoding a wild-type EGFR gene with isolated oligonucleotide primers corresponding to SEQ ID NO:7 and SEQ ID NO:8 in a polymerase chain reaction to form amplicon 4; and
      (iii) incorporating at least one label into amplicon 4 to form labeled amplicon 4.

2. The method of claim 1, wherein the sample is selected from the group consisting of urine, blood, cerebrospinal fluid, pleural fluid, sputum, peritoneal fluid, bladder washing, secretion, oral washing, tissue sample, touch prep and fine-needle aspirate.

3. The method of claim 1, wherein the sample comprises a tissue sample.

4. The method of claim 1, wherein the probe to chromosome 7 different from an EGFR(v3)-probe is selected from the group consisting of a chromosome enumeration probe, a chromosome arm probe, and an EGFR-probe.

5. The method of claim 1, wherein the probe to chromosome 7 different from an EGFR(v3)-probe is selected from the group consisting of a CEP 7 probe and an EGFR-probe.

6. The method of claim 1, wherein the set of chromosomal probes comprises at least one nucleic acid sequence lacking repetitive sequence elements.

7. The method of claim 1, wherein the set of chromosomal probes are fluorescently labeled.

8. The method of claim 1, wherein visualizing the hybridization pattern of the set of chromosomal probes in the plurality of cells of the sample is performed by fluorescence microscopy.

9. The method of claim 8, wherein fluorescence microscopy is performed with digital imaging.

10. A method of screening for the presence of EGFR(v3) in a sample, the method comprising:
   (a) obtaining a sample containing a plurality of cells;
   (b) hybridizing a set of chromosomal probes to the sample, wherein the set comprises an EGFR (v3)-probe and a probe to chromosome 7 different from an EGFR(v3)-probe; and
   (c) visualizing a hybridization pattern of the set of chromosomal probes in the plurality of cells of the sample, wherein the hybridization pattern comprises a presence of a signal from the probe to chromosome 7 different from an EGFR(v3)-probe and an absence of a signal from the EGFR(v3)-probe in at least one cell,
   wherein the probe to chromosome 7 different from an EGFR(v3)-probe is a CEP 7 probe,
   wherein the EGFR(v3)-probe is labeled amplicon 4 or amplicon 8 prepared according to the following procedure:
      (i) contacting a DNA comprising a sequence encoding a wild-type EGFR gene with a first set of isolated oligonucleotide primers corresponding to SEQ ID NO:7 and SEQ ID NO:8 or a second set of isolated oligonucleotide primers corresponding to SEQ ID NO:9 and SEQ ID NO:14;
      (ii) amplifying a portion of the sequence encoding a wild-type EGFR gene with the first set or second set of isolated oligonucleotide primers in a polymerase chain reaction to form amplicon 4 or amplicon 8, respectively; and (iii) incorporating at least one label into amplicon 4 or amplicon 8 to form labeled amplicon 4 or labeled amplicon 8, respectively.

11. The method of claim 10, wherein the sample is selected from the group consisting of urine, blood, cerebrospinal fluid, pleural fluid, sputum, peritoneal fluid, bladder washing, secretion, oral washing, tissue sample, touch prep and fine-needle aspirate.

12. The method of claim 10, wherein the sample comprises a tissue sample.

13. The method of claim 10, wherein the set of chromosomal probes comprises at least one nucleic acid sequence lacking repetitive sequence elements.

14. The method of claim 10, wherein the set of chromosomal probes are fluorescently labeled.

15. The method of claim 10, wherein visualizing the hybridization pattern of the set of chromosomal probes in the plurality of cells of the sample is performed by fluorescence microscopy.

16. The method of claim 15, wherein fluorescence microscopy is performed with digital imaging.

* * * * *

```
                        SEQUENCE LISTING

<160> NUMBER OF SEQ ID NOS: 14

<210> SEQ ID NO 1
<211> LENGTH: 37
<212> TYPE: DNA
<213> ORGANISM: Artificial Sequence
<220> FEATURE:
<223> OTHER INFORMATION: Synthetic oligonucleotide sequence

<400> SEQUENCE: 1
catcatccgc ggaaggatgc acaatcctac atgcccc                              37

<210> SEQ ID NO 2
<211> LENGTH: 39
<212> TYPE: DNA
<213> ORGANISM: Artificial Sequence
<220> FEATURE:
<223> OTHER INFORMATION: Synthetic sequence

<400> SEQUENCE: 2
catcatatcg atcctggtga acacaaccgg agaattaaa                            39

<210> SEQ ID NO 3
<211> LENGTH: 35
<212> TYPE: DNA
<213> ORGANISM: Artificial Sequence
<220> FEATURE:
<223> OTHER INFORMATION: Synthetic sequence

<400> SEQUENCE: 3
cggatcctgt gtacccatg tgtttaaatt tgctg                                 35

<210> SEQ ID NO 4
<211> LENGTH: 36
<212> TYPE: DNA
<213> ORGANISM: Artificial Sequence
<220> FEATURE:
<223> OTHER INFORMATION: Synthetic sequence

<400> SEQUENCE: 4
caggtacctt cttgggttag cagtgatcaa gtcaca                               36

<210> SEQ ID NO 5
<211> LENGTH: 36
<212> TYPE: DNA
<213> ORGANISM: Artificial Sequence
<220> FEATURE:
<223> OTHER INFORMATION: Synthetic sequence

<400> SEQUENCE: 5
caactagtat aaagcagaag catgtatcca ggttgc                               36
```

```
<210> SEQ ID NO 6
<211> LENGTH: 30
<212> TYPE: DNA
<213> ORGANISM: Artificial Sequence
<220> FEATURE:
<223> OTHER INFORMATION: Synthetic sequence

<400> SEQUENCE: 6
cctcgagcaa gccttggccc aggcttattc                                       30

<210> SEQ ID NO 7
<211> LENGTH: 40
<212> TYPE: DNA
<213> ORGANISM: Artificial Sequence
<220> FEATURE:
<223> OTHER INFORMATION: Synthetic sequence

<400> SEQUENCE: 7
catcatccgc ggcatgaaat ctgcattatc atcatctgca                            40

<210> SEQ ID NO 8
<211> LENGTH: 40
<212> TYPE: DNA
<213> ORGANISM: Artificial Sequence
<220> FEATURE:
<223> OTHER INFORMATION: Synthetic sequence

<400> SEQUENCE: 8
catcatatcg atgcatatgg acttactcaa atgttggcca                            40

<210> SEQ ID NO 9
<211> LENGTH: 35
<212> TYPE: DNA
<213> ORGANISM: Artificial Sequence
<220> FEATURE:
<223> OTHER INFORMATION: Synthetic sequence

<400> SEQUENCE: 9
cggatcctat agagtggctg acatcccta acgtg                                  35

<210> SEQ ID NO 10
<211> LENGTH: 25
<212> TYPE: DNA
<213> ORGANISM: Artificial Sequence
<220> FEATURE:
<223> OTHER INFORMATION: Synthetic sequence

<400> SEQUENCE: 10
cctcgagact tgccacggca gcgcc                                            25

<210> SEQ ID NO 11
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 11
catcgcggcc gcaccatttt catatttgag gaaagcatgg                            40

<210> SEQ ID NO 12
<211> LENGTH: 28
<212> TYPE: DNA
<213> ORGANISM: Artificial Sequence
<220> FEATURE:
<223> OTHER INFORMATION: Synthetic sequence
```

```
<400> SEQUENCE: 12
cctcgagtgg tggaggagcc gagggatc                                          28

<210> SEQ ID NO 13
<211> LENGTH: 40
<212> TYPE: DNA
<213> ORGANISM: Artificial Sequence
<220> FEATURE:
<223> OTHER INFORMATION: Synthetic sequence

<400> SEQUENCE: 13
catcgcggcc gcttctttgg ttcagctgag agaaacttgc                             40

<210> SEQ ID NO 14
<211> LENGTH: 30
<212> TYPE: DNA
<213> ORGANISM: Artificial Sequence
<220> FEATURE:
<223> OTHER INFORMATION: Synthetic sequence

<400> SEQUENCE: 14
cctcgagcag ggctcagcag gagacagagc                                        30
```